(12) United States Patent
Xiao

(10) Patent No.: US 11,083,814 B2
(45) Date of Patent: Aug. 10, 2021

(54) HEATING AND ATOMIZING AROMA DIFFUSER

(71) Applicant: Dongguan Hezhongchuan Electronic Technology Co., LTD., Dongguan (CN)

(72) Inventor: Yucheng Xiao, Shenzhen (CN)

(73) Assignee: DONGGUAN HEZHONGCHUAN ELECTRONIC TECHNOLOGY CO., LTD., Dongguan (CN)

( * ) Notice: Subject to any disclaimer, the term of this patent is extended or adjusted under 35 U.S.C. 154(b) by 121 days.

(21) Appl. No.: 16/285,184

(22) Filed: Feb. 25, 2019

(65) Prior Publication Data

US 2020/0237950 A1 Jul. 30, 2020

(30) Foreign Application Priority Data

Jan. 29, 2019 (CN) .......................... 201910085665.X

(51) Int. Cl.
*A61L 9/14* (2006.01)
*A61M 11/04* (2006.01)
(52) U.S. Cl.
CPC .............. *A61L 9/14* (2013.01); *A61M 11/042* (2014.02)

(58) Field of Classification Search
CPC ............ A61L 9/032; A61L 9/037; A61L 9/14; A61M 11/042
See application file for complete search history.

(56) References Cited

U.S. PATENT DOCUMENTS

| 6,106,786 A * | 8/2000 | Akahoshi | ................ A61L 9/122 222/187 |
| 7,499,632 B2 * | 3/2009 | Granger | .............. A01M 1/2033 392/386 |

\* cited by examiner

*Primary Examiner* — Timothy C Cleveland

(57) ABSTRACT

A heating and atomizing aroma diffuser includes a cover with an outlet thereof, an atomization core including a heating member and a liquid conduction member surrounding around the heating member, a spice storage, an airflow generator with an inlet thereof and a control unit. The inlet, the airflow generator, the spice storage, the atomization core and the outlet are connected to cooperatively form an air passageway thereof. The control unit is electrically connected to the heating member and the airflow generator to drive the heating member to generate heat, so that spice liquid adsorbed on a surface of the liquid conduction member is atomized into steam by high temperature, and then simultaneously drive the steam to diffuse into the air through the air passageway, thereby the steam can be diffused rapidly and sufficiently into the air, and has widespread spectrum and strong fragrance.

5 Claims, 4 Drawing Sheets

HEATING AND ATOMIZING AROMA DIFFUSER

BACKGROUND

1. Technical Field

The present disclosure generally relates to aroma diffusers field, and especially relates to a heating and atomizing aroma diffuser.

2. Description of Related Art

An aroma diffuser is a kind of machine for diffusing essential oils and filling the air with fragrance, which can keep bedrooms with high humidity, produce a certain amount of natural negative oxygen ions and purify the air to obtain the effects of aromatherapy. Furthermore, it not only can help to treat and to relieve diseases such as influenza, hypertension and bronchitis, but also can benefit for nervous systems, cardiovascular systems and metabolisms of the human body. Therefore, the aroma diffuser is more and more popular and used widely, such as hotels, bars, shops and families and other indoor places. However, such aroma diffuser in the market is worked mostly by means of natural evaporation or ultrasonic atomization. In this way, the evaporation speed of the fragrance is relatively slow so that the fragrance is weak.

SUMMARY

The technical problems to be solved: in view of the shortcomings of the related art, the present disclosure relates to a heating and atomizing aroma diffuser which can provide an atomization core to heat and atomizer spice liquid into steam by high temperature, and then the steam is simultaneously driven to diffuse into the air through its air passageway so that it can be diffused rapidly and thoroughly into the air, and has widespread spectrum and strong fragrance.

The technical solution adopted for solving technical problems of the present disclosure is:

A heating and atomizing aroma diffuser includes a cover including an outlet formed thereof, an atomization core connected to the outlet and including a heating member and a liquid conduction member surrounding around the heating member, a spice storage connected with the atomization core and configured to receive spices therein, the spices being liquid and adsorbed on a surface of the liquid conduction member, an airflow generator with a fan thereof connected to the atomization core and located on a side or a lower end of the atomization core, the airflow generator including an inlet for airflow generated by operating the fan passing through the inlet and then entering an air passageway, and a control unit electrically connected to the heating member and the airflow generator. The inlet, the airflow generator, the spice storage, the atomization core and the outlet are connected together to cooperatively form the air passageway thereof. The control unit is configured to drive the heating member to generate heat so that spice liquid adsorbed on the surface of the liquid conduction member is atomized into steam by high temperature, and then it can simultaneously drive the airflow generator to generate airflow which can drive the steam to diffuse into the air through the air passageway.

Wherein the heating and atomizing aroma diffuser further includes a frame tightly fixed with the cover and including a hollow post and a flat plate connected to the cover to form a first receiving room therebetween, the post including a second receiving room for receiving the atomization core therein, and the cover including a convex-downward first fixing portion sleevedly engaged with the post.

Wherein the heating and atomizing aroma diffuser further includes a base tightly fixed with the frame and including the control unit, an installing portion for receiving the airflow generator, a cooling storage connected with the atomization core and positioned below the atomization core for collecting coolant, and a clapboard formed between the installing portion and the cooling storage and configured to prevent the coolant from infiltrating into the airflow generator.

Wherein the spice storage is located in the first receiving room, and the flat plate includes a feeding passageway for adding the spices to the spice storage.

Wherein the post includes a through-hole attached to the surface of the liquid conduction member and connected with the spice storage, and the base includes a feeding inlet connected with the feeding passageway so that the spices can pass through the feeding passageway from the feeding inlet to enter the spice storage and then pass through the through-hole to infiltrate into the liquid conduction member, when adding spices.

Wherein the base further includes a coolant outlet for discharging the coolant generated by the cooling storage, and a first sealing ring formed between the feeding inlet and the feeding passageway and configured to prevent the spices from infiltrating into the cooling storage during adding the spices.

Wherein the coolant outlet is blocked by a first block for preventing the coolant from leaking outside during using the aroma diffuser; and the feeding inlet is blocked by a second block for preventing the spices from leaking outside during adding the spices.

Wherein the heating and atomizing aroma diffuser further includes a liquid container tightly fixed with the frame and including the spice storage and an opening connected to the atomization core, the liquid conduction member including a liquid conduction medium passing through the opening and then extending into the liquid container.

Wherein the flat plate further includes a second fixing portion protruding downwardly and extending into the opening to fixedly connect with the inner wall of the opening so as to tightly fix the frame and the liquid container.

Wherein the control unit is received in the first receiving room, and the flat plate is partially concave upward to form an installing portion of the airflow generator, with the inlet being located between the airflow generator and the liquid container.

The present disclosure provides the advantages as below.

The structure of the present disclosure is provided with the control unit electrically connected to the heating member and the airflow generator to drive the heating member to generate heat so that spice liquid adsorbed on a surface of the liquid conduction member is atomized into steam by high temperature, and then it can simultaneously drive the airflow generator to generate airflow which can drive the steam to diffuse into the air through the air passageway, which can diffuse rapidly and sufficiently into the air, and has widespread spectrum and strong fragrance.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating

DETAILED DESCRIPTION

Figure 1:
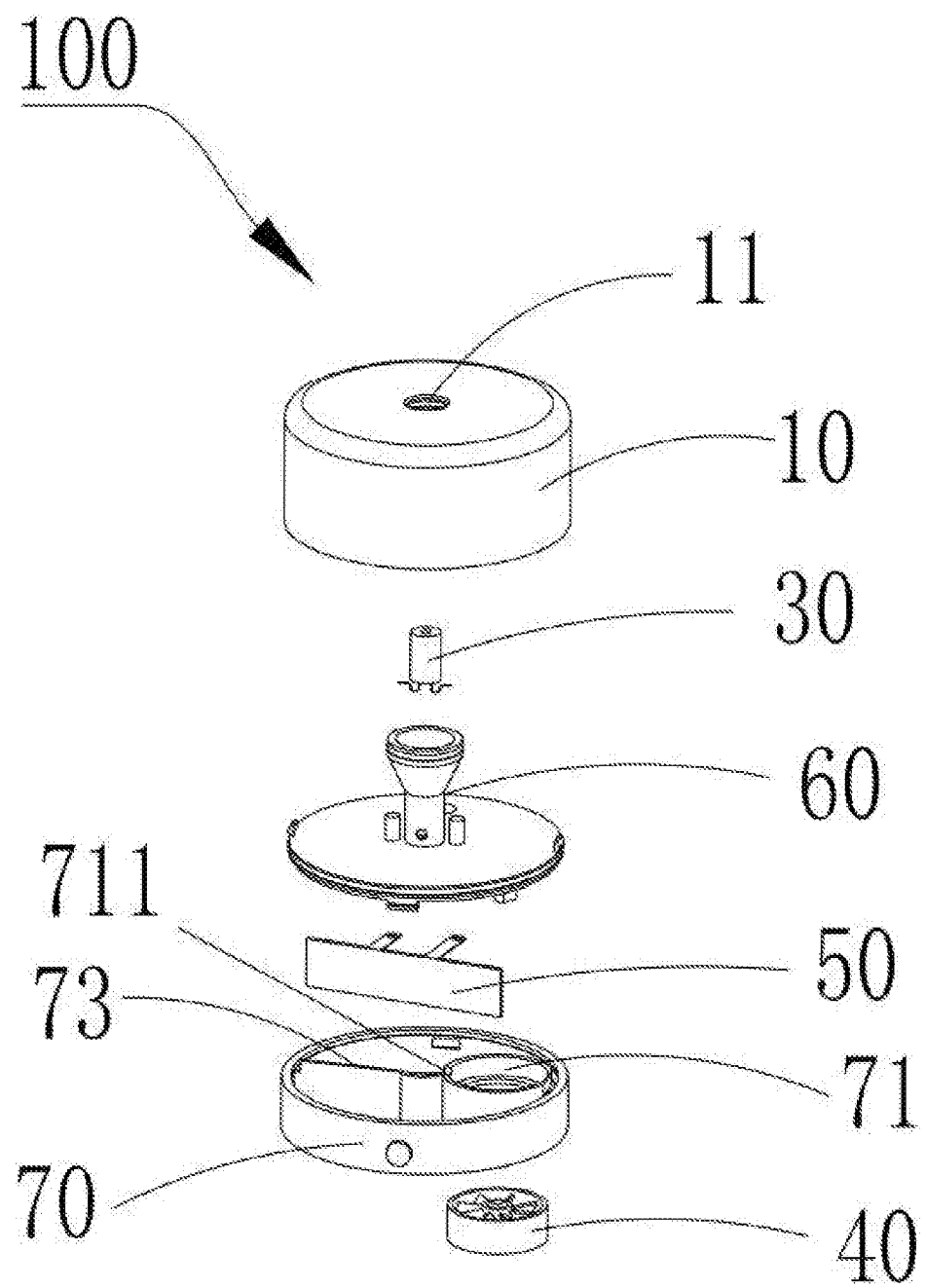
FIG. 1 is an exploded, schematic view of the heating and atomizing aroma diffuser in accordance with a first exemplary embodiment.

The disclosure is illustrated by way of example and not by way of limitation in the figures of the accompanying drawings, in which like reference numerals indicate similar elements. It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. It will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

In the description of the present disclosure, it needs to be explained that all the directional indicators (such as the terms: "upper", "below", "left", "right", "front", "back" . . . ), are shown in the specification of the present disclosure. The indicated orientation or position of the terms shown in the detailed description is based on the orientation or position shown in the figures of the accompanying drawings of the present disclosure, which is only to easily simplify the description of the present disclosure, but not indicated that the devices or elements of the present disclosure should have a particular orientation or should be designed and operated in a particular orientation. So the terms illustrated in the detail description are not by way of the limitation of the present disclosure.

In the description of the present disclosure, except where specifically otherwise illustrated or limited, the terms "connect" and "link" used herein should be understood in a broad sense. Such as, the meaning may be a tight connection, removable connection, or integrated connection. The meaning may also be a mechanical connection, electrical connection, direct connection or an indirect connection through intermediaries, or internal connection within two elements. The meaning of the terms used herein may be understood by one of ordinary skill in the related art according to specific conditions of the present disclosure.

Furthermore, in the description of the present disclosure, the terms such as "first" and "second" shown in the specification are only used to describe, but not indicated that the elements of the present disclosure is important or represented the amount of the elements. That is, the features limited by the terms of "first" and "second" may explicitly or implicitly include one or more features.

Figure 2:
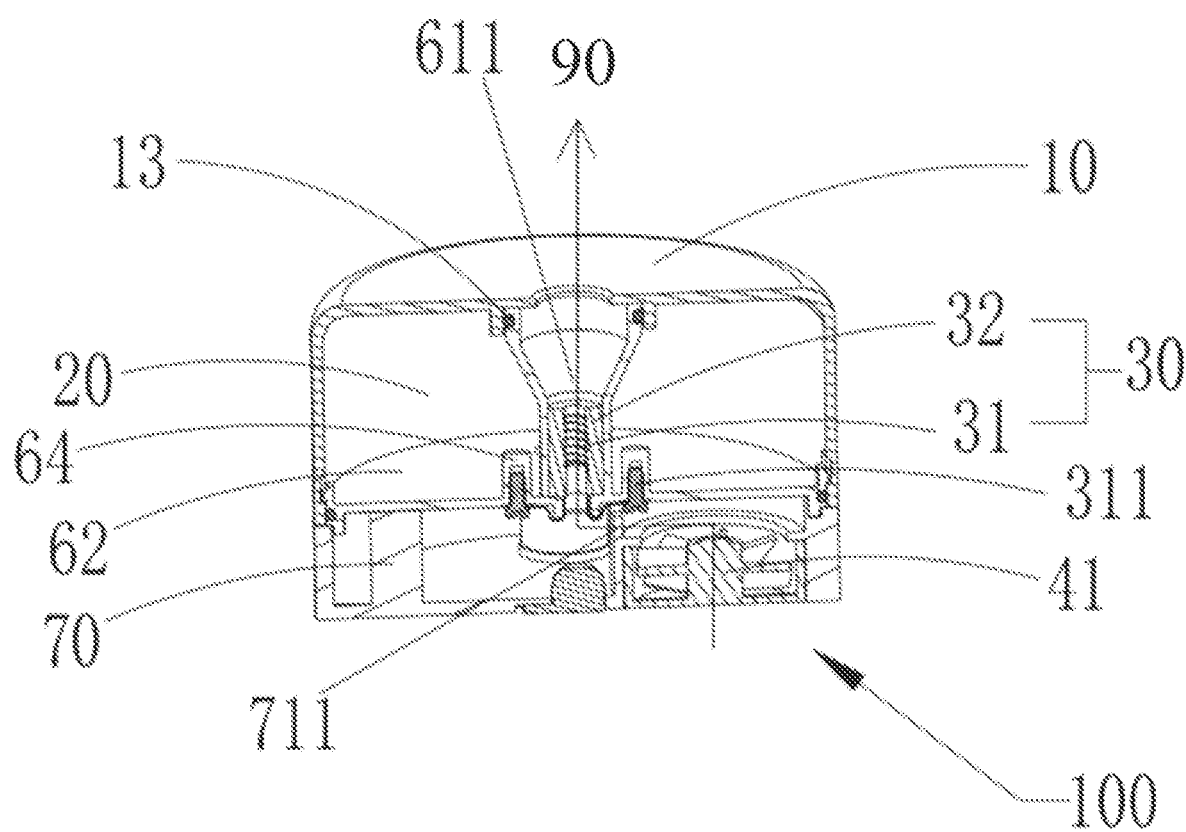
FIG. 2 is a cross-sectional view of the heating and atomizing aroma diffuser of FIG. 1.
Figure 3:
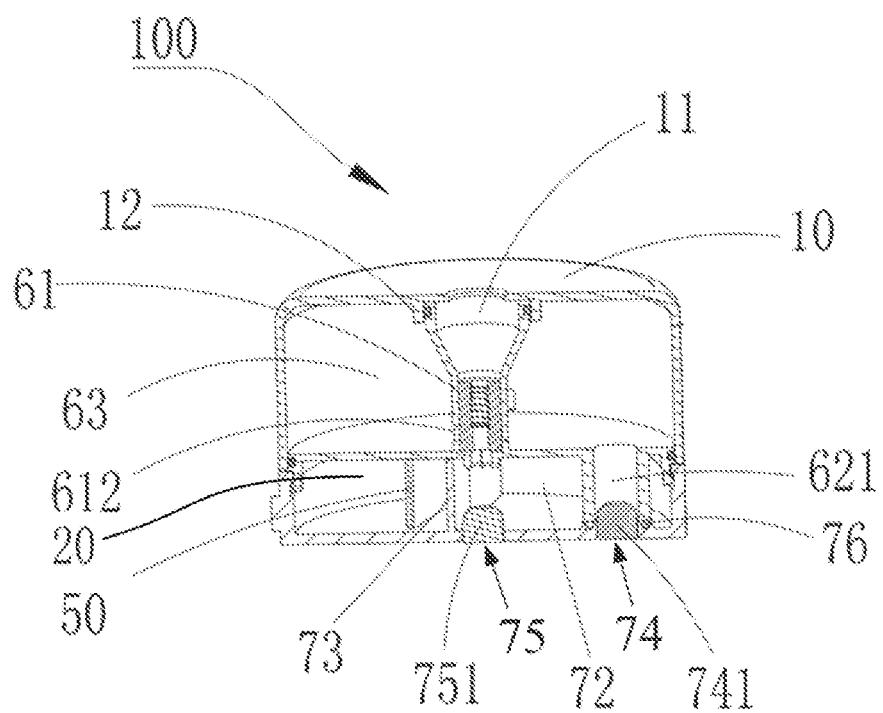
FIG. 3 is similar to FIG. 2, but shown from another view.

Referring to FIGS. 1-3, the heating and atomizing aroma diffuser 100 in accordance with an exemplary embodiment of the present disclosure includes a cover 10 which includes an outlet 11 formed thereof, an atomization core 30 connected to the outlet 11 and including a heating member 31 and a liquid conduction member 32 surrounding around the heating member 31, a spice storage 20 connected with the atomization core 30 and configured to receive spices therein, with the spices being liquid and adsorbed on a surface of the liquid conduction member 32, an airflow generator 40 with a fan 41 thereof connected to the atomization core 30 and located on a side or a lower end of the atomization core 30, the airflow generator 40 including an inlet 42 for airflow generated by operating the fan 41 passing through the inlet 42 and then entering an air passageway 90, and a control unit 50 electrically connected to the heating member 331 and the airflow generator 40. The inlet 42, the airflow generator 40, the spice storage 20, the atomization core 30 and the outlet 11 are connected together to cooperatively form the air passageway 90 thereof. The control unit 50 is configured to drive the heating member 31 to generate heat so that spice liquid adsorbed on the surface of the liquid conduction member 32 is atomized into steam by high temperature, and then it can simultaneously drive the airflow generator 40 to generate airflow which can drive the steam to diffuse into the air through the air passageway 90.

The heating and atomizing aroma diffuser 100 of the present disclosure includes the cover 10, the spice storage 20, the atomization core 30, the airflow generator 40 and the control unit 50. The cover 10 includes the outlet 11 and the airflow generator 40 includes the inlet 42 so that the inlet 42, the airflow generator 40, the spice storage 20, the atomization core 30 and the outlet 11 are connected together to cooperatively form the air passageway 90 thereof. The control unit 50 is electrically connected to the heating member 31 and the airflow generator 40 to drive the heating member 31 to generate heat, so that spice liquid adsorbed on the surface of the liquid conduction member 32 is atomized into steam by high temperature, and then it can simultaneously drive the airflow generator 40 to generate airflow which can drive the steam to diffuse into the air through the air passageway 90. Comparing to the conventional aroma diffuser, such structure can diffuse rapidly and sufficiently into the air, and has widespread spectrum and strong fragrance by the atomization core 30 heating and atomizing the spices.

In an exemplary embodiment of the present disclosure, the liquid conduction member 32 can be made of cotton or pore ceramics material. The spice can be essential oils or perfume and the heating member 31 can be a heating wire or a mesh heating wire.

In an exemplary embodiment of the present disclosure, the airflow generator 40 is a fan or other air suction devices.

Preferably, the heating and atomizing aroma diffuser 100 further includes a frame 60 tightly fixed with the cover 10 and including a hollow post 61 and a flat plate 62 connected to the cover 10 to form a first receiving room 63 therebetween. The post 61 includes a second receiving room 611 for receiving the atomization core 30 therein, and the cover 10 includes a convex-downward first fixing portion 12 sleevedly engaged with the post 61.

Furthermore, the post 61 includes a second sealing ring 13 formed on the outer wall thereof and resisted against the first fixing portion 12 to improve the sealing performance between the post 61 and the cover 10.

Referring to FIGS. 1-3, the heating and atomizing aroma diffuser 100 further includes a base 70 tightly fixed with the frame 60 by a threaded connection or an interference connection. The base 70 includes the control unit 50, an installing portion 71 for receiving the airflow generator 40, a cooling storage 72 connected with the atomization core 30 and positioned below the atomization core 30 for collecting coolant, and a clapboard 73 formed between the installing portion 71 and the cooling storage 72 and configured to prevent the coolant from infiltrating into the airflow generator 40, thereby it can not only keep the whole structure of the atomization core 30 dry, but also can ensure the heating and atomizing aroma diffuser 100 work normally.

Furthermore, the airflow generator 40 includes a recess 711 connected to the airflow generator 40 and the cooling storage 72 so that airflow generated by operating the airflow generator 40 can enter the cooling storage 72 through the recess 711 and then reach the atomization core 30.

Furthermore, the flat plate 62 includes a pair of third fixing portions 64 and the heating member 31 includes a connecting member 311 connected to the control unit 50 and received in the pair of third fixing portions 64, which can improve the connection stability between the heating member 31 and the control unit 50.

Preferably, the spice storage 20 is located in the first receiving room 63, and the flat plate 62 further includes a feeding passageway 621 for adding the spices to the spice storage 20.

Furthermore, the post 61 includes a through-hole 612 attached to the surface of the liquid conduction member 32 and connected with the spice storage 20. The base 70 includes a feeding inlet 74 connected with the feeding passageway 621 so that the spices can pass through the feeding passageway 621 from the feeding inlet 74 to enter the spice storage 20 and then pass through the through-hole 612 to infiltrate into the liquid conduction member 32, when adding the spices.

Furthermore, the base 70 further includes a coolant outlet 75 for discharging the coolant generated by the cooling storage 72, and a first sealing ring 76 formed between the feeding inlet 74 and the feeding passageway 621 and configured to prevent the spices from infiltrating into the cooling storage 72 during adding the spices.

Preferably, the coolant outlet 75 is blocked by a first block 751 for preventing the coolant from leaking outside during using the heating and atomizing aroma diffuser 100. When there is liquid contained in the cooling storage 72, the heating and atomizing aroma diffuser 100 can be temporarily suspended and the first block 751 can be removed to drain the fluid. The feeding inlet 74 is blocked by a second block 741 for preventing the spices from leaking outside during adding the spices.

Figure 4:
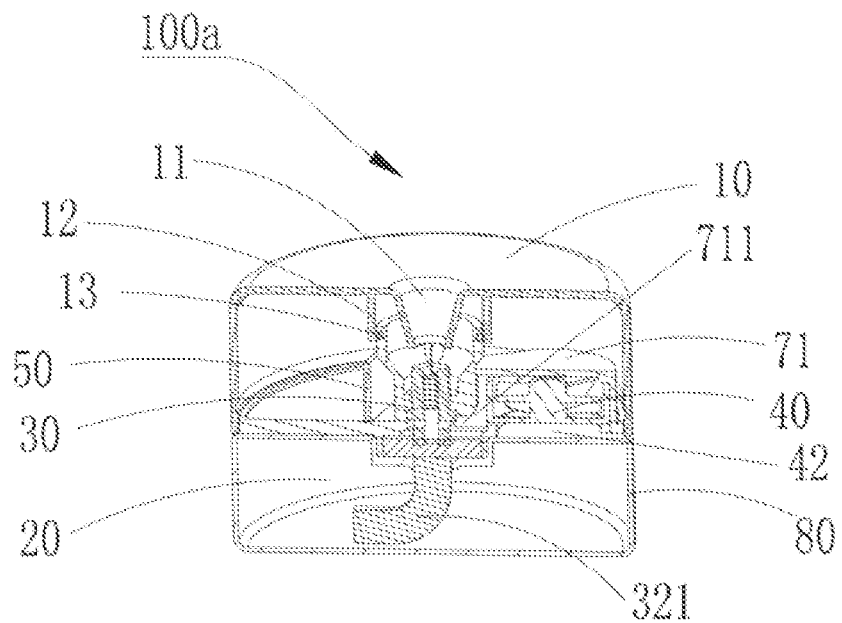
FIG. 4 is a cross-sectional view of the heating and atomizing aroma diffuser in accordance with a second exemplary embodiment.
Figure 5:
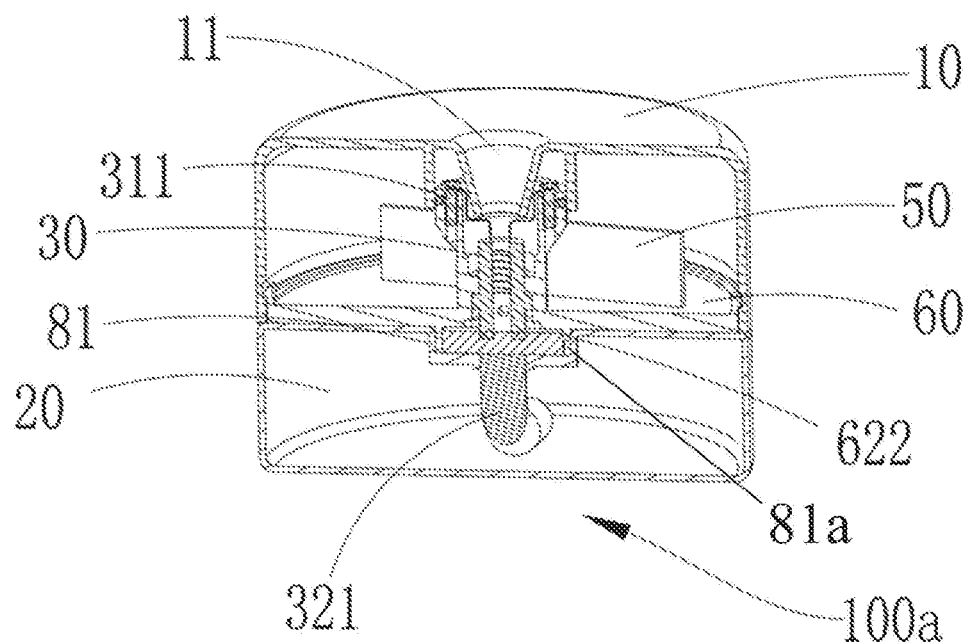
FIG. 5 is similar to FIG. 4, but shown from another view.

Referring to FIG. 4 and FIG. 5, the heating and atomizing aroma diffuser 100a according to another exemplary embodiment of the present disclosure includes a liquid container 80 tightly fixed with the frame 60. The liquid container 80 includes the spice storage 20 and an opening 81 connected to the atomization core 30, and the liquid conduction member 32 includes a liquid conduction medium 321 passing through the opening 81 and then extending into the liquid container 80. In this way, the spices in the liquid container 81 can be conducted into the liquid conduction member 32 via the liquid conduction medium 321.

Preferably, the flat plate 62 further includes a second fixing portion 622 protruding downwardly and extending into the opening 81 to fixedly connect with the inner wall of the opening 81 so as to tightly fix the frame 60 and the liquid container 80.

Preferably, the control unit 50 is received in the first receiving room 63, and the flat plate 62 is partially concave upward to form an installing portion 71 of the airflow generator 40. The inlet 42 is located between the airflow generator 40 and the liquid container 80 to ensure airflow generated by operating the airflow generator 40 entering the air passageway 90.

Furthermore, the airflow generator 40 includes a recess 711 connected to the airflow generator 40 and the atomization core 30 so that airflow generated by operating the airflow generator 40 can enter the atomization core 30 through the recess 711. When using the heating and atomizing aroma diffuser 100a, The control unit 50 is configured to drive the heating member 31 to generate heat so that spice liquid adsorbed on the surface of the liquid conduction member 32 is atomized into steam by high temperature, and then it can simultaneously drive the airflow generator 40 to generate airflow which can drive the steam to diffuse into the air through the air passageway 90.

In another exemplary embodiment of the present disclosure, during the heating and atomizing aroma diffuser 100 on work, the airflow direction is: the airflow enters from the inlet 42, reaches the cooling storage 72 via passing through the airflow generator 40 and the recess 711 in turn, and then passes through the atomization core 30, and finally discharges from the outlet 11.

In another exemplary embodiment of the present disclosure, during the heating and atomizing aroma diffuser 100a on work, the airflow direction is: the airflow enters from the inlet 42, reaches the atomization core 30 via passing through the airflow generator 40 and the recess 711 in turn, and finally discharges from the outlet 11.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A heating and atomizing aroma diffuser comprising:
a cover comprising an outlet formed thereof;
an atomization core connected to the outlet and comprising a heating member and a liquid conduction member surrounding around the heating member;
a spice storage connected with the atomization core and configured to receive spices therein, with the spices being liquid and adsorbed on a surface of the liquid conduction member;
an airflow generator with a fan thereof connected to the atomization core and located on a side or a lower end of the atomization core, the airflow generator comprising an inlet for airflow generated by operating the fan passing through the inlet and then entering an air passageway;
a control unit electrically connected to the heating member and the airflow generator; and wherein
the inlet, the airflow generator, the spice storage, the atomization core and the outlet are connected together to cooperatively form the air passageway thereof; the control unit is configured to drive the heating member to generate heat so that spice liquid adsorbed on the surface of the liquid conduction member is atomized into steam by high temperature, and then it can simultaneously drive the airflow generator to generate airflow which can drive the steam to diffuse into the air through the air passageway, wherein the heating and atomizing aroma diffuser further comprises a frame tightly fixed with the cover and comprising a hollow post and a flat plate connected to the cover to form a first receiving room therebetween, the post comprising a second receiving room for receiving the atomization core therein, and the cover comprising a convex-downward first fixing portion sleevedly engaged with the post, wherein the heating and atomizing aroma diffuser further comprises a base tightly fixed with the frame and comprising the control unit, an installing portion for receiving the airflow generator, a cooling storage connected with the atomization core and positioned below the atomization core for collecting coolant, the coolant being the atomized steam which has cooled, and a clapboard formed between the installing portion and the cooling storage and configured to prevent the coolant from infiltrating into the airflow generator.

2. The heating and atomizing aroma diffuser as claimed in claim 1, wherein the spice storage is located in the first receiving room, and the flat plate comprises a feeding passageway for adding the spices to the spice storage.

3. The heating and atomizing aroma diffuser as claimed in claim 2, wherein the post comprises a through-hole attached to the surface of the liquid conduction member and connected with the spice storage, and the base comprises a feeding inlet connected with the feeding passageway so that the spices can pass through the feeding passageway from the feeding inlet to enter the spice storage and then pass through the through-hole to infiltrate into the liquid conduction member, when adding the spices.

4. The heating and atomizing aroma diffuser as claimed in claim 3, wherein the base further comprises a coolant outlet for discharging the coolant generated by the cooling storage, and a first sealing ring formed between the feeding inlet and the feeding passageway and configured to prevent the spices from infiltrating into the cooling storage during adding the spices.

5. The heating and atomizing aroma diffuser as claimed in claim 4, wherein the coolant outlet is blocked by a first block for preventing the coolant from leaking outside during using the heating and atomizing aroma diffuser; and the feeding inlet is blocked by a second block for preventing the spices from leaking outside during adding the spices.

* * * * *